United States Patent [19]

Horrobin et al.

[11] Patent Number: 6,015,821
[45] Date of Patent: Jan. 18, 2000

[54] NICOTINIC ACID ESTERS AND PHARMACEUTICAL COMPOSITIONS CONTAINING THEM

[76] Inventors: David Frederick Horrobin, Scotia Pharmaceuticals Ltd., Efamol House, Woodbridge Meadows, Guildford, Surrey, GU1 1BA; Mehar Manku, Scotia Pharmaceuticals Ltd., Research and Development Centre, Kingstown Broadway, Kingstown Industrial Estate, Carlisle, CA3 0HA; Austin McMordie, Scotia Pharmaceuticals Ltd., Research & Development Centre, Kingstown Broadway, Kingstown Industrial Estate, Carlisle, CA3 0HA; Philip Knowles, Scotia Pharmaceuticals Ltd., Research & Development Centre, Kingstown Broadway, Kingstown Industrial Estate, Carlisle, CA3 0HA, all of United Kingdom; Peter Redden, Efamol Research Inc., Unit 2, Chapman Drive, Annapolis Industrial Estate, P.O. Box 818 Kentville, Nova Scotia, Canada, B4N 4H8; Andrea Pitt, Scotia Pharmaceuticals Ltd. Research & Devlopment Centre, Kingstown Broadway, Kingstown Industrial Estate, Carlisle, CA3 0HA, United Kingdom

[21] Appl. No.: 08/952,305

[22] PCT Filed: May 1, 1996

[86] PCT No.: PCT/GB96/01054

§ 371 Date: Mar. 3, 1998

§ 102(e) Date: Mar. 3, 1998

[87] PCT Pub. No.: WO96/34858

PCT Pub. Date: Nov. 7, 1996

[30] Foreign Application Priority Data

May 1, 1995 [GB] United Kingdom ................ 9508823
Aug. 21, 1995 [GB] United Kingdom ................ 9517107
Jan. 10, 1996 [GB] United Kingdom ................ 9600431

[51] Int. Cl.[7] .................... C07D 213/30; C07D 213/80; A61K 31/44
[52] U.S. Cl. ................ 514/355; 514/277; 546/315; 546/339
[58] Field of Search ................ 546/315.339; 514/355, 514/277

[56] References Cited

U.S. PATENT DOCUMENTS

| | | | |
|---|---|---|---|
| 2,291,816 | 12/1942 | Goldblatt | 188/77 R |
| 2,924,528 | 2/1960 | Barsky et al. | 426/601 |
| 2,993,063 | 7/1961 | Alsop et al. | 554/109 |
| 4,199,557 | 4/1980 | Kijima et al. | 424/266 |
| 4,268,426 | 5/1981 | Williams | 514/420 |
| 4,668,664 | 5/1987 | Rougier | 514/29 |
| 4,851,426 | 7/1989 | Ladkani et al. | 260/22 TN |
| 5,286,512 | 2/1994 | Klemann et al. | 426/611 |
| 5,321,145 | 6/1994 | Schaefer | 554/82 |

FOREIGN PATENT DOCUMENTS

| | | |
|---|---|---|
| 0 018 342 | 10/1980 | European Pat. Off. . |
| 0 057 797 | 8/1982 | European Pat. Off. . |
| 0 087 864 | 9/1983 | European Pat. Off. . |
| 161422 | 3/1985 | European Pat. Off. . |
| 0 139 480 | 5/1985 | European Pat. Off. . |
| 0 161 114 | 11/1985 | European Pat. Off. . |
| 0 173 478 | 3/1986 | European Pat. Off. . |
| 0 184 058 | 6/1986 | European Pat. Off. . |
| 0 056 189 | 8/1986 | European Pat. Off. . |
| 0 222 155 | 5/1987 | European Pat. Off. . |
| 0 246 540 | 11/1987 | European Pat. Off. . |
| 0 304 244 | 2/1989 | European Pat. Off. . |
| 0 319 126 | 6/1989 | European Pat. Off. . |
| 0 321 128 | 6/1989 | European Pat. Off. . |
| 0 393 920 | 10/1990 | European Pat. Off. . |
| 0 405 873 | 1/1991 | European Pat. Off. . |
| 0 405 874 | 1/1991 | European Pat. Off. . |
| 0 515 982 | 12/1992 | European Pat. Off. . |
| 0 574 312 | 12/1993 | European Pat. Off. . |
| 0 611 569 | 8/1994 | European Pat. Off. . |
| 0 675 103 | 10/1995 | European Pat. Off. . |
| M1782 | 4/1963 | France . |
| 57-067511 | 4/1982 | Japan . |
| 61-129190 | 6/1986 | Japan . |
| 2-129119 | 5/1990 | Japan . |
| 4-99784 | 3/1992 | Japan . |
| 5-051355 | 3/1993 | Japan . |
| 0 888 162 | 1/1962 | United Kingdom . |
| 1 135 647 | 12/1968 | United Kingdom . |
| 1 293 277 | 10/1972 | United Kingdom . |
| 1 493 098 | 11/1977 | United Kingdom . |
| 1 529 762 | 10/1978 | United Kingdom . |
| 1 556 197 | 11/1979 | United Kingdom . |
| WO 91/09831 | 7/1991 | WIPO . |
| WO 95/04030 | 2/1995 | WIPO . |
| WO 96/33155 | 10/1996 | WIPO . |

OTHER PUBLICATIONS

Kumokawa et al. "Gamma–linolenic acid derivatives as platelet aggregation inhibitors," *Chemical Abstracts*, vol. 105, No. 9, Sep. 1, 1986, Abstract No. 78532f.

(List continued on next page.)

*Primary Examiner*—Zinna Northington Davis
*Attorney, Agent, or Firm*—Bruce D. Gray; Kilkpatrick Stockton LLP

[57] ABSTRACT

Compounds, compositions, and methods of use as a pharmaceutical, where the compounds have structure (I), where B is —C(=O)— or —CH$_2$—O—, C is a direct bond or is a diol residue, a hydroxy-substituted carboxylic acid residue, or a dicarboxylic acid residue, and D is a fatty acid residue or a fatty alcohol residue, where the acid residues or alcohol residues for ester linkages with the corresponding alcohols or acids.

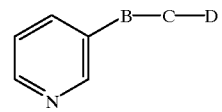

8 Claims, No Drawings

OTHER PUBLICATIONS

"Trienoic fatty acid pyridylmethyl esters," *Chemical Abstracts,* vol. 101, No. 19, Nov. 5, 1984, Abstract No. 171104v.

S. Koori et al., "Unsaturated higher aliphatic esters of nicotinic acid," *Chemical Abstracts,* vol. 77, No. 25, Dec. 18, 1972, Abstract No. 164488f.

L.J. Deterding et al., "Fast–bombardment and tandem mass spectrometry for determining structures of fatty acids as their picolyl ester derivatives," *Analytica Chimica Acta,* vol. 200, No. 1, 1987, pp. 431–445.

K. Kimura et al., "Higher unsaturated fatty alcohol esters having antiulcer activity," *Chemical Abstracts,* vol. 87, No. 7, Aug. 15, 1977, Abstract No. 53462e.

O. Bertelsen et al., "Structural elucidation of alkyl–branched chain aliphatic alcohols and fatty acids by mass spectrometry of their respective alkyl nicotinate and picolinylcarboxylate derivatives," *Fette, Seifen, Anstrichmittel,* vol. 87, No. 9, 1985, pp. 336–342.

W.W. Christie et al., "Mass spectra of the picolinyl esters of isomeric mono– and dienoic fatty acids," *Lipids,* vol. 22, No. 4, 1987, pp. 224–228.

V. Spitzer et al., "Curupira tefeensis. Part 2. Occurence of acytylenic fatty acids," *Fett Wissenschaft Technologie—Fat Science Technology,* vol. 93, No. 5, 1991, pp. 169–174.

Breusch et al, Darstellung der di–, tri–und terta–homologen Reihen der Methan–Methylol–Fettsaureester, *Chemische Berichte,* vol. 88, (1955) pp. 1511–1519.

Deterding, L., et al., "Fast–Atom–Bombardment and Tandem Mass Spectrometry for Determining Structures of Fatty Acids and Their Picolyl Ester Derivatives," *Chemical Abstracts,* 110:38801, 1987.

Deterding, L, et al., "Tandem Mass Spectrometry for Identifying Fatty Acid Derivatives that Undergo Charge–Remote Fragmenations," *Chemical Abstracts,* 110:56917, 1988.

Harvey, D.J., Picolinyl Derivatives for the structural Determination of Fatty Acids by Chemical Abstracts 101:166564, 1984.

Harvey, D.J., "Pyridine–Containing Derivatives for the Structural Elucidationof the Alkyl Chains of Lipids by Mass Spectrometry and a Comparison with the Spectra of Related Heterocyclic Derivatives," *Chemical Abstracts,* 114:206360, 1990.

Jie, et al., "Mass Spectra of Picolinyl Ester Derivatives of Some Conjugated Diacetylenic Fatty Acids," *Chemical Abstracts,* 118:191384, 1992.

Lagen, et al. "Inhibition of Proliferation of Ehrlich Ascites Carcinoma Cells in Vitro and In Vivo by Halogen Analogs of Long Chain Acyl– and Alkyglycerols," *Chemical Abstracts,* vol. 92, No. 1, Jan. 7, 1980, Abstract No. 461a.

Vajdi, M. et al., GC/MS Analysis of Some Long Chain Esters, Ketones and Propanediol Diesters, *Chemical Abstracts,* vol. 95, No. 5, Aug. 3, 1981, Abstract No. 4167e.

Watanabe et al., "Preparation and Formulation of Orally Active Aminoglycoside Antibiotics," *Chemical Abstracts,* vol. 107, No. 3 Jul. 20, 1987, Abstracts No. 23659p.

NICOTINIC ACID ESTERS AND PHARMACEUTICAL COMPOSITIONS CONTAINING THEM

This application is a 371 of PCT/GB96/01054 filed May 1, 1996.

FIELD OF THE INVENTION

The invention relates to new esters and to compositions for pharmaceutical uses, particularly for managing cardiovascular diseases, inflammatory diseases, dermatological disorders including baldness, diabetes, cancer, psychiatric disorders and other appropriate medical and nutritional disorders.

BACKGROUND

Blood Cholesterol

There is considerable background in relation to the specific matter of blood cholesterol levels. As discussed in EPA 0 087 864, essential fatty acids (EFAs), particularly gammalinolenic acid (GLA) and dihomogammalinolenic acid (DGLA), act to lower blood cholesterol levels, the mechanism being unknown; these acids of course are the starting materials for 1-series PG synthesis, the bodily conversions of EFAs generally being as set out in Table 1 below:

TABLE 1

| n-6 EFA's | | n-3 EFA's |
|---|---|---|
| 18:2n-6 (Linoleic acid, LA) | | 18:3n-3 (α-Linolenic acid, ALA) |
| ↓ | δ-6-desaturase | ↓ |
| 18:3n-6 (γ-Linolenic acid, GLA) | | 18:4n-3 (Stearidonic acid, SA) |
| ↓ | elongation | ↓ |
| 20:3n-6 (Dihomo-γ-linolenic acid, DGLA) | | 20:4n-3 |
| ↓ | δ-5-desaturase | ↓ |
| 20:4n-6 (Arachidonic acid, AA) | | 20:5n-6 (Eicosapentaenoic acid, EPA) |
| ↓ | elongation | ↓ |
| 22:4n-6 (Adrenic acid) | | 22:5n-3 |
| ↓ | δ-4-desaturase | ↓ |
| 22:5n-6 | | 22:6n-3 (Docosahexaenoic acid, DHA) |

The acids, which in nature are of the all-cis configuration, are systematically named as derivatives of the corresponding octadecanoic, eicosanoic or docosanoic acids, e.g. z,z-octadeca-9,12-dienoic acid or z,z,z,z,z,z-docosa-4,7,10,13,16,19-hexaenoic acid, but numerical designations based on the number of carbon atoms, the number of centres of unsaturation and the number of carbon atoms from the end of the chain to where the unsaturation begins, such as, correspondingly, 18:2n-6 or 22:6n-3 are convenient. Initials, e.g., EPA and shortened forms of the name e.g. eicosapentaenoic acid are used as trivial names in some of the cases.

As also discussed in EPA 0 087 864, there are a number of agents which lower cholesterol levels in the blood by binding to bile salts in the gastro-intestinal tract and directly enhancing cholesterol excretion in the faeces. Illingworth et al in the Lancet for Feb. 7, 1981 pp 296–7 report use of the bile salt binder colestipol, plus nicotinic acid (niacin) against an inherited high blood-cholesterol condition, with "dramatic" effect. No mechanism is discussed, the article suggesting simply that therapy, in addition to taking binders, may best be directed towards reducing lipoprotein synthesis, and saying that niacin has been reported to do that.

Niacin is one of the two forms of Vitamin B3, the other being niacinamide; by an unknown mechanism it acts systematically to lower cholesterol levels in blood without any substantial effect on cholesterol excretion.

The effect of niacin is believed to be due to an effect it has in stimulating prostaglandin (PG) synthesis, specifically $PGE_1$ synthesis from dihomogammalinolenic acid and $PGD_2$ synthesis from arachidonic acid, as part of a mechanism that leads to reduced cholesterol synthesis and hence reduced levels in the blood. It is for example known that $PGE_1$ stimulates the formation of cyclic AMP (adenosine monophosphate) and that cyclic AMP inhibits cholesterol synthesis. Further, niacin, in addition to its blood cholesterol lowering effect, causes flushing and tingling, effects that the inventor has noted are also among those of stimulating prostaglandin synthesis, particularly $PGE_1$ and $PGD_2$ synthesis.

Niacinamide, in contrast, though generally equivalent in its bodily effects to niacin, does not show this stimulating effect on PG synthesis, nor does it cause flushing and tingling or show a blood cholesterol lowering effect. Linkage of these facts as instances of the unusual existence of differences in properties between niacin and niacinamide, supports the view that PG levels and blood cholesterol levels are linked.

BACKGROUND

Microcirculation

More recently, and quite separately from questions of blood cholesterol level, it has become apparent that many disease states may involve partial reductions in blood flow in the micro circulation. Such reduced microcirculatory flow has been reported or presumed to be important in diabetes, in cardiovascular diseases, in inflammatory diseases, in dermatological disorders including baldness, in cancer and in various other disorders. Particularly in cancer, partial or complete shutdown of the capillary bed may be important in preventing expected responses to treatment using such agents as radiation, chemotherapy or photodynamic therapy. The effects of niacin and fatty acids, especially EFAs, on the microcirculation are to maintain normal capillary flow, partly by unknown mechanisms and partly by the stimulation of the formation of vasodilator substances such as prostaglandins $E_1$ and $D_2$ and nitric oxide. The EFAs themselves, particularly GLA, DGLA and EPA and DHA are also of value in reducing damage to normal tissues during radiotherapy as described in patents EP-A-0,416,855 and EP-A-0,609,064. Thus niacin-EFA derivatives of the types discussed hereinafter are of particular value in association with radiotherapy because they may enhance the damaging effects of radiation on the tumour while at the same time reducing the damaging effects on normal tissues. Many chemotherapeutic agents used in cancer also cause severe side effects and the niacin-EFA derivatives may be used in managing these also.

THE INVENTION

The invention concerns niacin compounds both as such when new, and in relation to the indications discussed above, in respect of which it proposes administration of niacin as the compounds.

Such administered compound may be an ester:

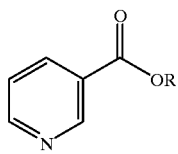

where R is a fatty acid alcohol chain —$CH_2$—$R^1$, $R^1$ being the carbon chain of an n-6 or n-3 essential or other $C_{12}$ or longer chain fatty acid $R^1COOH$, particularly GLA, DGLA or AA of the n-6 series, or EPA or DHA of the n-3 series.

Other directly linked compounds of value are esters of niacin alcohol (3-pyridyl carbinol) with the fatty acids, niacin alcohol being considered herein as included within the broad term niacin.

The invention extends further to esters of niacin with "extended" fatty acids where a fatty acid forms a monoester of a diol and the other hydroxy function of the diol is esterified to the niacin (alternatively a niacin monoester of the diol may be formed and then reacted with the fatty acid). In such 'extended' esters R in the formula above is:

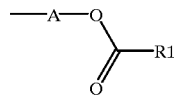

where $R^1$ is as before and A is a diol residue.

Three other classes of "extended" compounds are, for example, possible:
  (i) niacin and fatty acid alcohol linked through a hydroxycarboxylic acid residue.
  (ii) niacin alcohol and fatty acid linked through a hydroxycarboxylic acid residue.
  (iii) niacin alcohol and fatty alcohol linked through a dicarboxylic acid residue.

The general formula is then:

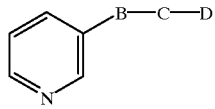

where B is —C(=O)— (nicotinic acid) or —$CH_2$—O— (niacin alcohol), C which is optional is a diol or hydroxy carboxylic acid or dicarboxylic acid residue, and D is a fatty acid or fatty acid alcohol residue, the links between B and C and C and D being ester links.

A particularly suitable diol is 1,3-dihydroxy propane (2-deoxy glycerol), well tolerated in the body, but broadly a diol or other "link" may be any pharmacologically acceptable compound giving suitable pharmacokinetics in the ester, including release of the niacin and fatty acid in the body, and desirably non-chiral. A diol may thus have a cyclic or non-cyclic structure, with or without hetero-atoms and saturated or unsaturated, but especially a hydrocarbon structure —$(CH)_n$— where n=1 to 10. The corresponding use of 1-carboxy-3-hydroxypropane or 1,3-dicarboxypropane (malonic acid) or corresponding compounds to form the extended molecules in classes (i)–(iii) is appropriate.

All of the compounds discussed contain one or more ester linkages. The preparation of these compounds may be achieved by any reasonable method of ester synthesis and especially:

(i) by reaction of an alcohol with the acid chloride, acid anhydride or other suitable acid derivative with or without the presence of an organic tertiary base, e.g. pyridine, in a suitable inert solvent, e.g. methylene chloride, and at a temperature between 0° C. and 120° C.

(ii) by reaction of an alcohol with the acid or a short or medium chain length ester of the acid, in the presence of a suitable acid catalyst, e.g. p-toluenesulphonic acid, with or without a suitable inert solvent, e.g. toluene, at a temperature between 50° C. and 180° C. such that the water or alcohol formed in the reaction is removed, e.g. by azeotropy or under vacuum.

(iii) by reaction of an alcohol with the acid in the presence of a condensing agent, e.g. 1,3-dicyclohexylcarbodiimide with or without a suitable base, e.g. 4-(N,N-dimethylamino) pyridine, in an inert solvent, e.g. methylene chloride, at a temperature between 0° C. and 50° C.

(iv) by reaction of an alcohol with the acid or a short or medium chain length ester of the acid, or an activated ester thereof, e.g. vinyl, trifluoroethyl, in the presence of a hydrolase enzyme, e.g. hog liver esterase, with or without a suitable solvent, e.g. hexane at temperatures between 20° C. and 80° C. under conditions such that the water or alcohol by-product formed in the reaction is removed from the reaction mixture, e.g. molecular sieves, vacuum.

(v) by reaction of the acid with a suitable alcohol derivative, e.g. tosylate, iodide, with or without the presence of a suitable base, e.g. potassium carbonate, in a suitable inert solvent, e.g. dimethylformamide, and at a temperature between 0° C. and 180° C.

(vi) by reaction of an acid ester (acid-$CO_2Y$) with the alcohol in the presence of a catalytic amount of an alkoxide of type $M^+OY^-$ where M is an alkali or alkaline earth metal, e.g. sodium, and Y is an alkyl group containing 1–4 carbon atoms which may be branched, unbranched, saturated or unsaturated. The reaction is carried out with or without a suitable solvent, e.g. toluene, at temperatures between 50° C. and 180° C. such that the lower alcohol, HOY, is removed from the reaction mixture, e.g. by azeotropy or vacuum.

The value of the esters and other derivatives is believed to be in bringing the niacin and essential fatty acid (or alcohol) to bear together, or possibly in enhancing transport of the niacin in the body by virtue of the lipophilic fatty acid carbon chain or "tail". In the latter case, the fatty acid can be other than GLA, DGLA or AA or the other specified acids, which themselves can be taken separately or used as a vehicle for the niacin ester.

In pharmaceutical terms there is a particular value in combining two active ingredients within a single molecule. With a mixture of two active ingredients directed at a particular clinical indication, regulatory authorities would normally require trials of placebo compared to each active ingredient separately as well as the two together. When the two actives are part of a single molecule, the actives will not usually have to be tested separately, so greatly reducing the complexity and cost of clinical trials. Thus irrespective of any synergistic interactions there is pharmaceutical value in combining niacin with one of the fatty acids in a single molecule. Many of the compounds are however to our knowledge novel and are claimed as such, irrespective of their particular use.

Dose Ranges

Suitable amounts of active materials are:

Niacin compound, (calculated as niacin): 10 mg–20 g, preferably 0.5 g to 10 g and very preferably 1 to 5 g daily;

together with the corresponding amount of fatty acid or fatty acid alcohol required by the stoichiometry of the compound.

Pharmaceutical Presentation

The compositions according to the invention are conveniently in a form suitable for oral, rectal, parenteral or topical administration in a suitable pharmaceutical vehicle, as well known generally for any particular kind of preparation.

Advantageously a preservative is incorporated into the preparations e.g. alpha-tocopherol in a concentration of about 0.1% by weight has been found suitable for the purpose. Alternatively, the materials of European patent application EP-A-0 577 305 may be used.

The niacin esters are liquid at normal temperatures and may be presented as such or with other oily carriers or diluents in any appropriate form. Such forms would include soft or hard gelatin capsules, tabletted dry forms, emulsions, liposomes, liquids, enteral or parenteral preparations or any other form known to those skilled in the art.

As one specific example, four soft gelatin capsules containing niacin as its ester with GLA alcohol, 0.5 g, may be administered thrice daily in the treatment of any appropriate disease and in particular the diseases mentioned earlier. Alternatively the same material may be presented as an emulsion, for example, using phospholipids or galactolipids as emulsifiers, or as a topical product containing 0.01% to 20% of the niacin ester. Any of the other compounds noted may be presented in similar ways using techniques known to those skilled in the art.

SYNTHESIS

The following examples illustrate the invention.

EXAMPLE 1 z,z,z-octadeca-6,9,12-trienyl nicotinate

Ester of Niacin and GLA Alcohol 1,3-Dicyclohexylcarbodiimide (97 g, 0.49 mol) and 4-(N,N-dimethylamino)pyridine (65 g, 0.53 mol) in methylene chloride (800 ml) were added with stirring to a solution of nicotinic acid (60 g, 0.49 mol) and z,z,z-octadeca-6,9,12-trienol (107 g, 0.41 mol) in methylene chloride (1200 ml). The progress of the reaction was monitored by tlc. On completion, the reaction mixture was filtered and the organic layer washed with 2M hydrochloric acid (500 ml) and water (3×500 ml), dried with magnesium sulphate and concentrated under reduced pressure. Purification by dry column chromatography using a gradient of ethyl acetate in hexane yielded z,z,z-octadeca-6,9,12-trienyl nicotinate as a pale yellow oil in 91% yield.

EXAMPLE 2 z,z,z-eicosa-8,11,14-trienyl nicotinate

Ester of Niacin and DGLA Alcohol

Prepared as in the above method but replacing z,z,z-octadeca-6,9,12-trienol with z,z,z-eicosa-8,11,14-trienol. The product was obtained as a pale yellow oil in 79% yield.

EXAMPLE 3

1-(z,z,z-octadeca-6,9,12-trienoyloxy)-3-(nicotinyloxy)-propane $C_3$-linked Diester of Niacin and GLA 1,3-Dicyclohexylcarbodiimide (211 g, 1.02 mol) and 4-(N,N-dimethylaminopyridine (141 g, 1.15 mol) in methylene chloride (2000 ml) were added with stirring to a solution of nicotinic acid (131 g, 1.07 mol) and 1-(z,z,z-octadeca-6,9,12-trienyloxy)-3-hydroxypropane (300 g, 0.89 mol) in methylene chloride (2000 ml). The progress of reaction was monitored by tlc. On completion, the reaction mixture was filtered and the organic layer washed with 2M hydrochloric acid (2000 ml) and water (3×2000 ml), dried with magnesium sulphate and concentrated under reduced pressure. Purification by dry column chromatography using a gradient of ethyl acetate in hexane yielded 1-(z,z,z-octadeca-6,9,12-trienoyloxy)-3-(nicotinyloxy)-propane as a pale yellow oil in 81% yield.

To prepare the 1-(z,z,z-octadeca-6,9,12-trienoyloxy)-3-hydroxypropane used, a solution of z,z,z-octadeca-6,9,12-trienoic acid (150 g) in methylene chloride (500 ml) was added dropwise to a mixture of 1,3-dihydroxypropane (205 g), 1,3-dicyclohexylcarbodiimide (130 g) and 4-(N,N-dimethylamino)pyridine (87 g) in methylene chloride (2500 ml) at room temperature under nitrogen. When tlc indicated that the reaction had gone to completion, the reaction mixture was filtered. The filtrate was washed with dilute hydrochloric acid, water and saturated sodium chloride solution. The solution was dried, concentrated and purified by dry column chromatography to yield 1-(z,z,z-octadeca-6,9,12-trienoyloxy)-3-hydroxypropane as a pale yellow oil.

EXAMPLE 4

(3-Pyridyl)methyl-(z,z,z-octadeca-6,9,12-trienoate)

Ester of Niacin Alcohol and GLA

A mixture of 1,3-dicyclohexylcarbodiimide (33.55 g, 0.1623 mol), 4-(N,N-dimethylamino)pyridine (19.87 g, 0.1626 mol), z,z,z-octadeca-6,9,12-trienoic acid (37.67 g, 0.1355 mol) and 3-pyridyl carbinol (17.70 g, 0.1622 mol) were stirred as a solution in methylene chloride (1 liter) under a nitrogen atmosphere at room temperature. The progress of the reaction was followed by t.l.c. On completion, the reaction mixture was filtered and the organic layer washed with 2M HCl (1 liter), water (1 liter), saturated sodium bicarbonate solution (1 liter) and water (2×1 liter). The organic layer was dried over anhydrous sodium sulphate, filtered and stripped to dryness under reduced pressure. Purification by flash chromatography (ethyl acetate/hexane) yielded the title compound as a clear, pale yellow oil.

EXAMPLE 5

(z,z,z-octadeca-6,9,12-trienoyloxy)(3-nicotinyloxy) methane $C_1$ Linked Diester of Niacin and GLA Part 1: Chloro(z,z,z-octadeca-6,9,12-trienoyloxy)methane Anhydrous zinc chloride (88 mg) was added to a mixture of z,z,z-octadeca-6,9,12-trienoyl chloride (34.7 mmol) and paraformaldehyde (34.7 mmol). The mixture was stirred under an atmosphere of nitrogen at room temperature for 30 minutes. The reaction was then equipped with a reflux condenser and calcium chloride drying tube and heated at 90° C. for 6 hours. After completion of the reaction as shown by tlc, the mixture was diluted with hexane and purified by flash chromatography to give chloro-(z,z,z-octadeca-6,9,12-trienoyloxy)methane as a clear oil.

Part 2: (z,z,z-octadeca-6,9,12-trienoyloxy)(3-nicotinyloxy) methane

To a solution of niacin (0.306 mmol) in 400 µl of dry pyridine with stirring in an atmosphere of nitrogen was added chloro(z,z,z-octadeca-6,9,12-trienoyloxy)methane (0.306 mmol) and triethylamine (0.303 mmol). The mixture was heated at 80° C. for 5 hours after which tlc indicated the reaction had gone to completion. The pyridine was evaporated and the residue dissolved in chloroform, washed with water, dried, concentrated and purified by flash column chromatography to give (z,z,z-octadeca-6,9,12-trienoyloxy)(3-nicotinyloxy)methane as a clear oil.

EXAMPLE 6

(z,z,z,z,z-eicosa-5,8,11,14,17-pentaenoyloxy)(3-nicotinyloxy)methane $C_1$ Linked Diester of Niacin and EPA Part 1: chloro(z,z,z,z,z-eicosa-5,8,11,14,17-pentaenoyloxy)methane z,z,z,z,z-eicosa-5,8,11,14,17-pentaenoyl chloride (28 mmol) was reacted with paraformaldehyde (28 mmol) under the same conditions as given in Example 5, Part 1 to give chloro(z,z,z,z,z-eicosa-5,8,11,14,17-pentaenoyloxy)methane as a clear oil.

Part 2: (z,z,z,z,z-eicosa-5,8,11,14,17-pentaenoyloxy)(3-niconinyloxy)methane

Niacin (0.286 mmol) was reacted with chloro(z,z,z,z,z-eicosa-5,8,11,14,17-pentaenoyloxy)methane (0.286 mmol) under the same conditions as Example 5, Part 2 to give (z,z,z,z,z-eicosa-5,8,11,14,17-pentaenoyloxy)(3-nicotinyloxy)methane as a clear oil.

EXAMPLE 7

(±)-1-(z,z,z,-octadeca-6,9,12-trienoyloxy)-1-(3-nicotinyloxy)ethane $C_1$, (Methyl Substituted) Linked Diester of Niacin and GLA Part 1: (±)-1-chloro-1-(z,z,z-octadeca-6,9,12-trienoyloxy)ethane Anhydrous zinc chloride (300 mg) was added to z,z,z-octadeca-6,9,12-trienoyl chloride (120 mmol). Acetaldehyde (120 mmol) was added dropwise with stirring over 30 minutes in an ice bath under an atmosphere of nitrogen. The reaction mixture was then stirred at room temperature for an additional 40 minutes and was shown to be complete by tlc. Water was added and the mixture was extracted twice with diethyl ether. After drying the solvent was evaporated to give (±)-1-chloro-1-(z,z,z-octadeca-6,9,12-trienoyloxy)ethane as a clear oil.

Part 2: (±)-1-(z,z,z-octadeca-6,9,12-trienoyloxy)-1-(3-nicotinyloxy)ethane

To a solution of niacin (29 mmol) in 30 ml of dry pyridine with stirring in an atmosphere of nitrogen was added (±)-1-chloro-1-(z,z,z-octadeca-6,9,12-trienoyloxy)ethane (29 mmol) and triethylamine (29 mmol). The mixture was heated at 80° C. for 5 hours after which time tlc indicated the reaction had gone to completion. The pyridine was evaporated and the residue dissolved in chloroform, washed with water, dried, concentrated and purified by flash column chromatography to give (±)-1-(z,z,z-octadeca-6,9,12-trienoyloxy)-1-(3-nicotinyloxy)ethane as a clear oil.

EXAMPLE 8

(3-pyridyl)methyl-(z,z,z-octadeca-6,9,12-trienyl)-succinate

Diester of Niacin Alcohol and GLA Alcohol with Succinic Acid

Part 1: z,z,z-octadeca-6,9,12-trienyl succinate (ester of GLA alcohol and succinic acid).

A solution of z,z,z-octadeca-6,9,12-trienol (2 g, 7.56 mmol) and succinic anhydride (757 mg, 7.56 mmol) in tetrahydrofuran (40 ml) was prepared at room temperature and cooled to 0° C. To this was added dropwise with stirring a solution of DBU (1.15 g, 7.56 mmol) in tetrahydrofuran (20 ml) under an atmosphere of nitrogen. On completion of the reaction as shown by tlc, the mixture was diluted with diethyl ether (100 ml), washed with 2M hydrochloric acid (2×100 ml), water (2×100 ml) and saturated sodium chloride solution (2×100). The organic phase was dried with magnesium sulfate, filtered and concentrated under reduced pressure to yield z,z,z-octadeca-6,9,12-trienyl succinate as a pale yellow oil.

Part 2: (3-pyridyl)methyl-(z,z,z-octadeca-6,9,12-trienyl)-succinate (diester of niacin alcohol and GLA alcohol with succinic acid).

z,z,z-octadeca-6,9,12-trienyl succinate (1.50 g, 4.11 mmol) in methylene chloride (10 ml) was added dropwise with stirring to a solution of 3-pyridylcarbinol (0.45 g, 4.11 mmol), 1,3-dicyclohexylcarbodiimide (0.93 g, 4.53 mmol) and 4-(N,N-dimethylamino)pyridine (0.65 g, 5.35 mmol) in methylene chloride (10 ml) at room temperature under an atmosphere of nitrogen. On completion of the reaction as shown by tlc, the mixture was filtered, concentrated under reduced pressure and purified by flash column chromatography (chloroform) to yield (3-pyridyl)methyl-(z,z,z-octadeca-6,9,12-trienyl)-succinate as a pale yellow oil.

EXAMPLE 9 z,z,z-octadeca-6,9,12-trienyl-(2-nicotinyloxy)acetate

Diester of Nicotinic Acid and GLA Alcohol with Glycolic Acid

Part 1: z,z,z-octadeca-6,9,12-trienyl-(2-chloro)acetate (chloroacetyl ester of GLA alcohol).

To an ice-cooled solution of z,z,z-octadeca-6,9,12-trienol (2 g, 7.56 mmol) and triethylamine (2.02 g, 20 mmol) in methylene chloride (20 ml) was added dropwise with stirring chloroacetyl chloride (1.13 g, 10 mmol) in methylene chloride (20 ml) under an atmosphere of nitrogen. On completion of the reaction as shown by tlc, the mixture was washed with water (2×100 ml) and saturated sodium chloride solution (100 ml). The organic phase was dried with magnesium sulfate, filtered and concentrated under reduced pressure. Toluene (100 ml) was added to azeotropically remove final traces of water. z,z,z-octadeca-6,9,12-trienyl-(2-chloro)acetate was obtained as a dark brown oil.

Part 2: cesium nicotinate (cesium salt of nicotinic acid).

Nicotinic acid (0.86 g, 7 mmol) and cesium carbonate (1.14 g, 3.5 mmol) were swirled in methanol (60 ml) until a clear solution resulted. Methanol was removed in vacuo to yield cesium nicotinate as a white solid.

Part 3: z,z,z-octadeca-6,9,12-trienyl-(2-nicotinyloxy)acetate (diester of nicotinic acid and GLA alcohol with glycolic acid).

Cesium nicotinate (1.79 g, 7 mmol) and z,z,z-octadeca-6,9,12-trienyl-(2-chloro)acetate (2.39 g, 7 mmol) were stirred overnight at room temperature in anhydrous N,N-dimethylformamide (70 ml) under an atmosphere of nitrogen. On completion of the reaction as shown by tlc, the mixture was partitioned between hexane (160 ml) and saturated sodium chloride solution (200 ml). The aqueous phase was back extracted with hexane (160 ml) and the combined hexane layers were washed with saturated sodium chloride solution (200 ml). The organic phase was dried with magnesium sulfate and concentrated under reduced pressure to yield z,z,z-octadeca-6,9,12-trienyl-(2-nicotinyloxy)acetate as a brown oil.

We claim:

1. A compound of the structure:

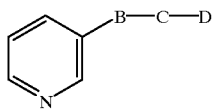

wherein B is selected from the group consisting of —C(=O)— and —CH$_2$—O—, C is selected from the group consisting of a diol residue a hydroxy-substituted carboxylic acid residue and a dicarboxylic acid residue, with the proviso that when B is —CH$_2$—O—, C is not a diol residue, D is selected from the group consisting of a fatty acid residue and a fatty alcohol residue, wherein the acid residues or alcohol residues form ester linkages with the corresponding alcohols or acids.

2. A compound according to claim 1, wherein the fatty acid or fatty acid alcohol residue is a residue of an n-6 or n-3 essential or other C$_{12}$ or longer chain fatty acid.

3. A compound according to claim 1, wherein C has one, two or three carbon atoms.

4. A compound according to claim 2, wherein the fatty acid or fatty acid alcohol residue is GLA, DGLA, or AA of the n-6 series or is EPA or DHA of the n-3 series.

5. A pharmaceutical composition comprising one or more compounds of claim 1, 2, or 3, and a pharmaceutically acceptable carrier.

6. A nutritional or skin care composition for oral, parenteral, or topical administration, comprising one or more compounds of claim 1, 2, or 3, together with a suitable pharmaceutically acceptable carrier.

7. A method of managing cardiovascular diseases, inflammatory diseases, dermatological disorders including baldness, diabetes, cancer, psychiatric disorders and other appropriate medical and nutritional disorders comprising administering to a patient in need thereof an effective amount of the compound according to claim 1, 2 or 3.

8. A method for the management of radiotherapy for cancer, or of chemotherapy for cancer comprising administering to a patient in need thereof an effective amount of the compound according to claim 1, 2, or 3.

* * * * *